United States Patent [19]

Rüger et al.

[11] Patent Number: 4,933,346

[45] Date of Patent: Jun. 12, 1990

[54] DIARYLALKYL PIPERAZINE DERIVATIVES, A PROCESS FOR THEIR PREPARATION, THEIR USE, AND MEDICAMENTS CONTAINING THEM

[75] Inventors: Wolfgang Rüger, Kelkheim; Hansjörg Urbach, Kronberg/Taunus; Joachim Kaiser, Frankfurt am Main, all of Fed. Rep. of Germany

[73] Assignee: Hoechst Aktiengesellschaft, Frankfurt am Main, Fed. Rep. of Germany

[21] Appl. No.: 192,666

[22] Filed: May 10, 1988

[30] Foreign Application Priority Data

May 12, 1987 [DE] Fed. Rep. of Germany ....... 3715763

[51] Int. Cl.$^5$ ................. A61K 31/495; A61K 31/445; A61K 31/40; C07D 295/08
[52] U.S. Cl. ..................................... 514/255; 514/183; 514/210; 514/212; 514/317; 514/428; 540/450; 540/575; 540/609; 544/396; 544/398; 546/236; 548/575; 548/576; 548/950
[58] Field of Search ............... 544/358, 396, 403, 398; 514/255

[56] References Cited

U.S. PATENT DOCUMENTS 4,370,329 1/1983 Scherm et al. ...................... 514/255
4,766,125 8/1988 Van Daele ........................... 514/255

FOREIGN PATENT DOCUMENTS 504202 7/1981 Spain .

Primary Examiner—Cecilia Shen
Attorney, Agent, or Firm—Finnegan, Henderson, Farabow, Garrett and Dunner

[57] ABSTRACT

Compounds I are described

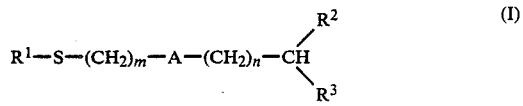

with $R^1$ equal to (cyclo)alk(en)yl or

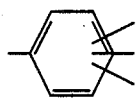

$R^2/R^3$ equal to phenyl or phenylalkyl,
A equal to

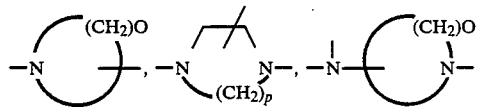

m equal to 2–4, and
n equal to 1–4.

Compounds I and their salts are calcium antagonists.

6 Claims, No Drawings

DIARYLALKYL PIPERAZINE DERIVATIVES, A PROCESS FOR THEIR PREPARATION, THEIR USE, AND MEDICAMENTS CONTAINING THEM

The invention relates to diarylalkyl-substituted alkylamines, to a process for their preparation, to their use as medicines, and to medicaments containing them.

Many diarylbutylpiperidine and diarylbutylpiperazine derivatives are, by reason of their action as dopamine antagonists, used therapeutically as neuroleptics. Structurally related compounds from the series of benzhydrylpiperazine and diarylbutylpiperazine derivatives act as inhibitors of the influx of calcium ions into cells, such as, for example, cinnarizine, flunarizine and lidoflazine. They are used as therapeutics for the treatment of cardiovascular and cerebrovascular disorders.

N-Arylpiperazine alkanamides with diarylbutyl substituents of piperazine systems are described in European Patent Application No. 68,544: they improve the blood supply to the heart and protect it from the consequences of an episode of ischemia, anoxia or hypoxia.

Spanish Patent No. 504,202 describes benzhydrylpiperazine derivatives in which, however, the benzhydryl group is always directly bonded to one nitrogen of the piperazine, not via a $(CH_2)_n$ bridge. Moreover, these compounds show merely a vasodilator action, but no calcium-antogonistic action.

Hence, it was surprising that the compounds of the present invention impede to an unusually great extent the influx of calcium ions into cells. Hence they are suitable as therapeutics for the treatment of various diseases, especially of the cardiovascular system.

The present invention is directed at compounds of the formula I $$R^1-S-(CH_2)_m-A-(CH_2)_n-CH\diagup^{R^2}_{\diagdown R^3} \qquad (I)$$

which have excellent calcium-antagonistic actions and in which $R^1$ denotes $(C_1-C_6)$-alkyl, straight-chain or branched, $(C_3-C_8)$-cycloalkyl, $(C_2-C_6)$-alkenyl, straight-chain or branched, $(C_5-C_8)$-cycloalkenyl,

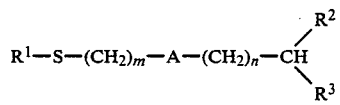

in which $R^4$, $R^5$ and $R^6$ denote, identically or differently and independently of one another, hydrogen, $(C_1-C_6)$-alkyl, $(C_3-C_8)$-cycloalkyl, hydroxyl, $(C_1-C_4)$-alkoxy, $(C_1-C_4)$-alkylthio, F, Cl, Br, I, nitro, cyano, trifluoromethyl, formyl, carboxyl, $(C_1-C_6)$-alkoxycarbonyl, $(C_1-C_6)$-acyl, carbamoyl, N-mono- or N,N-di-$(C_1-C_6)$-alkylcarbamoyl, sulfo, $(C_1-C_6)$-alkoxysulfonyl, sulfamoyl, N-mono- or N,N-di-$(C_1-C_6)$-alkylsulfamoyl, $(C_1-C_6)$-alkylsulfinyl, $(C_1-C_6)$-alkylsulfonyl, amino, unsubstituted or substituted with one or two identical or different $(C_1-C_6)$-alkyl, $(C_1-C_6)$-acyl or aryl, preferably phenyl, groups, $R^2$ and $R^3$ denote, identically or differently and independently of one another, phenyl, phenyl-$(C_1-C_4)$-alkyl, the phenyl ring in each case being unsubstituted or substituted by one, two or three substitutents from the group comprising $(C_1-C_4)$-alkyl, $(C_1-C_4)$-alkoxy, F, Cl, Br, I, cyano, nitro or trifluoromethyl, A denotes an amine

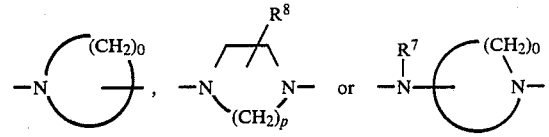

in which $R^7$ denotes hydrogen, $(C_1-C_6)$-alkyl, or aryl, preferably phenyl, $R^8$ denotes hydrogen, $(C_1-C_6)$-alkyl, formyl, $(C_1-C_6)$ acyl, carboxyl, $(C_1-C_6)$-alkoxycarbonyl, carbamoyl, N-mono- or N,N-di-$(C_1-C_6)$-alkylcarbamoyl, o denotes 3, 4, 5, 6 or 7, p denotes 2 or 3, m denotes 2, 3 or 4, and n denotes 1, 2, 3 or 4, and the salts of the compounds of the formula I with physiologically tolerated acids.

Preferred compounds of the formula I are those in which at least one of the radicals and indices has the following meaning:

$R^1$ $(C_3-C_8)$-cycloalkyl,

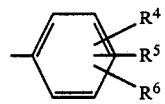

in which $R^4$, $R^5$ and $R^6$ denote, identically or differently and independently of one another, hydrogen, $(C_1-C_6)$-alkyl, $(C_1-C_4)$-alkoxy, $(C_1-C_4)$-alkylthio, F, Cl, Br, I, nitro, cyano, trifluoromethyl, formyl, carboxyl, $(C_1-C_6)$-alkoxycarbonyl, $(C_1-C_6)$-acyl, carbamoyl, N-mono- or N,N-di-$(C_1-C_6)$-alkylcarbamoyl, sulfo, sulfamoyl, N-mono- or N,N-di-$(C_1-C_6)$-alkylsulfamoyl, $(C_1-C_6)$-alkylsulfinyl or $(C_1-C_6)$-alkylsulfonyl, $R^2$ and $R^3$ denote, identically or differently and independently of one another, phenyl, phenylmethyl, the phenyl ring in each case being unsubstituted or substituted by one, two or three substituents from the group comprising methyl, ethyl, methoxy, ethoxy, F, Cl, Br, I, cyano, nitro or trifluoromethyl, A denotes an amine

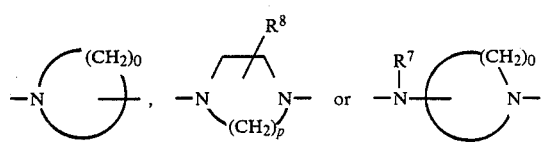

in which $R^7$ denotes hydrogen, methyl or ethyl, $R^8$ denotes hydrogen, carboxyl or carbamoyl, o denotes 4, 5 or 6, p denotes 2 or 3, m denotes 2, 3 or 4, and n denotes 1, 2, 3 or 4, and the salts of the compounds of the formula I with physiologically tolerated acids.

Particularly preferred compounds of the formula I are those in which at least one of the substituents and indices has the following meaning:
$R^1$ ($C_5$-$C_7$)-cycloalkyl,

in which
$R^4$, $R^5$ and $R^6$ denote, identically or differently and independently of one another, hydrogen, methyl, ethyl, propyl, isopropyl, n-butyl, sec-butyl, isobutyl, tert.butyl, methoxy, ethoxy, methylthio, fluorine, chlorine, bromine iodine, nitro, cyano, trifluoromethyl, acetyl, methylsulfonyl or methylsulfinyl,
$R^2$ and $R^3$ denote, identically or differently and independently of one another, phenyl, phenylmethyl, in each case the phenyl ring being unsubstituted or substituted by one, two or three substituents from the group comprising methyl, fluorine, chlorine, bromine, cyano, nitro or trifluoromethyl,
A denotes an amine

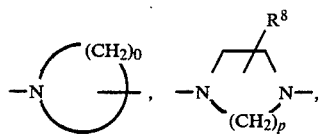

in which
$R^8$ denotes hydrogen, carboxyl or carbamoyl,
o denotes 4, 5 or 6,
p denotes 2 or 3,
m denotes 2, 3 or 4, and
n denotes 2, 3 or 4,
and the salts of the compounds of the formula I with physiologically tolerated acids.

Very particularly preferred compounds of the formula I are those in which at least one of the substituents or indices has the following meaning:
$R^1$

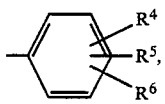

in which
$R^4$, $R^5$ and $R^6$ denote, identically or differently and independently of one another, hydrogen, methyl, tert.butyl, methoxy, methylthio, fluorine, chlorine, bromine, nitro, cyano, trifluoromethyl, acetyl, methylsulfonyl or methylsulfinyl,
$R^2$ and $R^3$ denote, identically or differently and independently of one another, phenyl, phenylmethyl, in each case the phenyl ring being unsubstituted or substituted by fluorine or trifluoromethyl,
A denotes an amine

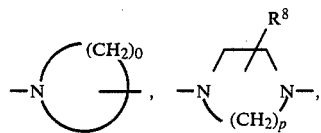

in which
$R^8$ denotes hydrogen,
o denotes 5,
p denotes 2,
m denotes 2, and
n denotes 3,
and the salts of the compounds of the formula I with physiologically tolerated acids.

Examples of suitable acids of this type are inorganic acids such as hydrochloric acid, hydrobromic acid, hydroiodic acid, sulfuric acid, phosphoric acid or nitric acid, or organic acids such as tartaric acid, citric acid, malic acid, lactic acid, maleic acid, fumaric acid, malonic acid, oxalic acid, acetic acid, propionic acid, methanesulfonic acid, benzenesulfonic acid, p-toluenesulfonic acid, naphthalene-1,5-disulfonic acid or gluconic acid.

Some of the compounds of the formula I have asymmetric carbon atoms and may thus occur as enantiomers and diastereomers. The invention embraces both the pure enantiomers and the racemates. The racemates can be separated into the enantiomers by conventional methods, for example by salt-formation with optically active acids such as camphorsulfonic acid or dibenzoyltartaric acid, fractional crystallization, followed by liberation of the bases from their salts, or by derivatization with suitable optically active reagents, separation of the diastereomeric derivatives by fractional crystallization or chromatography on silica gel or alumina, and cleavage again. The diastereomers can be separated by conventional methods, such as fractional crystallization or column chromatography.

The present invention also relates to a process for the preparation of compounds of the formula I, which comprises (a) reacting a compound of the formula II $$R^1-S-(CH_2)_m-Y \qquad (II)$$

in which $R^1$ and m have the same meaning as in formula I, and which Y denotes a leaving group which can be displaced nucleophilically, in particular a Cl, Br or I atom or a sulfonic acid radical, preferably a methanesulfonyl, benzenesulfonyl, p-toluenesulfonyl or trifluoromethanesulfonyl radical, with a compound of the formula III

in which $R^2$, $R^3$ and n have the same meaning as in formula I, and in which Z denotes

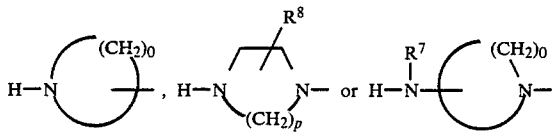

in which
R⁷, R⁸, o and p have the same meaning as in formula I, under the conditions of a nucleophilic substitution, preferably in a polar organic solvent such as an alcohol, preferably methanol, ethanol, propanol or isopropanol, or a lower ketone, preferably acetone, methyl ethyl ketone or methyl isobutyl ketone, or in acetonitrile, dimethylformamide, dimethyl sulfoxide or sulfolane, or a hydrocarbon, preferably toluene, with or without the presence of an auxiliary base to capture the acid which is formed, preferably in the presence of potassium carbonate, sodium carbonate, triethylamine, pyridine, 1,5-diazabicyclo[5.4.0]undec-5-ene or 1,5-diazabicyclo[4.3.0]non-5-ene, with or without the presence of an alkali metal halide, preferably sodium iodide or potassium iodide, at a temperature between 0° and 160° C., preferably between 20° and 120° C., or (b) reacting a compound of the formula IV $$R^1-S-(CH_2)_m-Z \qquad (IV)$$

in which $R^1$ and m have the same meaning as in formula I, and Z has the same meaning as in formula III, with a compound of the formula V

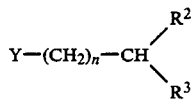

in which $R^2$, $R^3$ and n have the same meaning as in formula I and Y has the same meaning as in formula II,
under the conditions of a nucleophilic substitution, as described under (a),
or (c) reacting a compound of the formula VI $$R^1-SH \qquad (VI)$$

in which $R^1$ has the same meaning as in formula I, with a compound of the formula VII

in which $R^2$, $R^3$, A, m and n have the same meaning as in formula I, and Y has the same meaning as in formula II, either in a polar aprotic solvent such as acetonitrile, tetrahydrofuran, dimethyl sulfoxide, dimethylformamide, sulfolane or N-methylpyrrolidone, in the presence of a strong base, such as sodium hydride, potassium hydride, sodamide, lithium diisopropylamide, butyllithium or lithium hexamethyldisilazide, preferably in dimethylformamide or dimethyl sulfoxide in the presence of sodium hydride or sodamide, at a temperature between −40° and +100° C., preferably between −20° and +50° C., or in a protic or aprotic polar organic solvent such as a lower alcohol, for example methanol, ethanol or isopropanol, or a lower ketone, preferably acetone, methyl ethyl ketone or methyl isobutyl ketone, or in dimethylformamide, in the presence of a weak to moderately strong base, such as an alkali metal or alkaline earth metal hydroxide or carbonate, preferably sodium carbonate or potassium carbonate, or an amine such as, for example, triethylamine, pyridine, N-ethyldiisopropylamine, 1,5-diazabicyclo[5.4.0]undec-5-ene or 1,5-diazabicyclo[4.3.0]non-5-ene, at a temperature between 0° and 160° C., preferably between 20° and 120° C., (d) reacting a compound of the formula VIII $$R^1-W \qquad (VIII)$$

in which $R^1$ has the same meaning as in formula I, and in which W denotes a leaving group which can be displaced nucleophilically, in particular a fluorine, chlorine, bromine or iodine atom, a nitro, hydroxyl, alkoxy or trialkylammonium group, or a sulfonic acid radical, preferably a fluorine or chlorine atom, a nitro group or a methanesulfonyl, benzenesulfonyl, p-toluenesulfonyl or trifluoromethanesulfonyl radical, with a compound of the formula IX

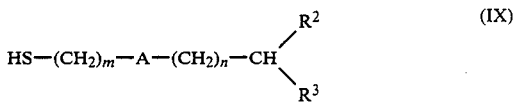

in which $R^2$, $R^3$, A, m and n have the same meaning as in formula I, under the conditions of a nucleophilic substitution, for example without solvent or in an aqueous solvent, preferably in a polar organic solvent, such as an alcohol, preferably methanol, ethanol, propanol or isopropanol, or a ketone, preferably acetone, methyl ethyl ketone or methyl isobutyl ketone, or an ether, preferably diethyl ether, tert.butyl methyl ether, dimethoxyethane, tetrahydrofuran or dioxane, or a halogenated hydrocarbon, preferably dichloromethane, chloroform or 1,2-dichloroethane, or in acetonitrile, dimethylformamide, dimethyl sulfoxide or sulfolane, or in a hydrocarbon, preferably benzene or toluene, or in a mixed aqueous-organic solvent system with the addition of a phase-transfer catalyst, with or without the presence of an auxiliary base to capture the acid which is formed, preferably in the presence of potassium carbonate, sodium carbonate, triethylamine, pyridine, lithium diisoproplamide, n-butyllithium, sodium hydride, potassium hydride, sodamide, 1,5-diazabicyclo[5.4.0]undec-5-ene or 1,5-diazabicyclo[4.3.0]non-5-ene, with or without the presence of copper powder, at a temperature between −80° and +200° C., preferably between −30° and +120° C.

The compounds of the formula II are known from the literature or can be prepared under analogous conditions from compounds of the formula VI by reaction with α,ω-dihalogenoalkanes or ω-halogenoalkyl sulfonates.

The preparation of the compounds of the formula III has been proposed in German Patent Application P No. 36 00 390.5, as follows:

The compounds of the formula III with Z equal to

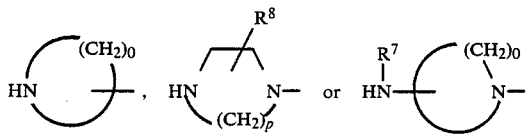

in which $R^7$, $R^8$, o and p have the same meaning as in formula I, can be prepared in a manner known per se from compounds of the formula X

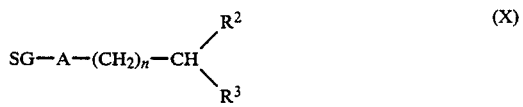

in which $R^2$, $R^3$, A and n have the same meaning as in formula I, and in which SG denotes a suitable protective group such as, for example, a carbamate, amide, alkyl or benzyl group, preferably a formyl, ethoxycarbonyl, benzyl or trityl group, by elimination of the protective group under conditions known from the literature, for example acid or alkaline cleavage or hydrogenolysis.

The compounds of the formula III, with Z equal to

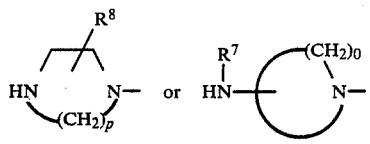

in which $R^7$, $R^8$, o and p have the same meaning as in formula I, can also be prepared by reaction of compounds of the formula V with amines of the formula Z—H, Z being one of the abovementioned groups, under the conditions of a nucleophilic substitution as described under process variant (a), or by reaction of compounds of the formula V with protected amines

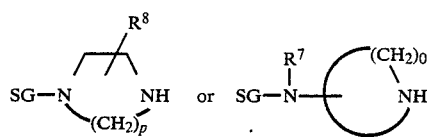

in which $R^7$, $R^8$, o and p have the same meaning as in formula I and SG has the same meaning as in formula X, under the conditions of a nucleophilic substitution as described under process variant (a), with subsequent elimination of the protective group under customary conditions, for example by acid or alkaline cleavage or by hydrogenolysis.

The compounds of the formula III, in which Z is

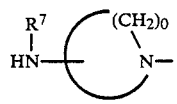

in which o has the same meaning as in formula I, and $R^7$ is methyl, can preferably be prepared by reduction with suitable reducing agents, preferably lithium aluminum hydride, from compounds of the same formula but in which $R^7$ denotes an alkoxy carbonyl radical.

The compounds of the formula IV can be prepared from compounds of the formula II by processes analogous to those already described for the preparation of compounds of the formula III from the compounds of the formula V, from compounds of the formula XI $$R^1-S-(CH_2)_m-A-SG \qquad (XI)$$

in which $R^1$, A and m have the same meaning as in formula I, and SG has the same meaning as in formula X, by elimination of the protective group under the customary conditions, for example by acid or alkaline cleavage or by hydrogenolysis, or from compounds of the formula VI by reaction with compounds of the formula XII $$Y-(CH_2)_m-A-SG \qquad (XII)$$

in which A and m have the same meaning as in formula I, Y has the same meaning as in formula II, and SG has the same meaning as in formula X, under the conditions of an alkylation reaction as described under process variant (c), followed by an elimination of the protective group under the customary conditions.

Most of the compounds of the formula V and VI are known from the literature or can be prepared in analogous manner.

The preparation of compounds of the formula VII has been proposed in German Patent Application P No. 36 00 390.5, as follows:

The compounds of the formula VII can be prepared from the compounds of the formula III by reaction with α,ω-dihalogenoalkanes or ω-halogenoalkyl sulfonates under the conditions of a nucleophilic substitution as described under process variant (a), or from the compounds of the formula V by reaction with a compound of the formula XIII $$Y-(CH_2)_m-Z \qquad (XIII)$$

in which m has the same meaning as in formula I, Y has the same meaning as in formula II, and Z has the same meaning as in formula III, under the conditions of a nucleophilic substitution as described under process variant (a), or from compounds of the formula V by reaction with a compound of the formula XIV $$HO-(CH_2)_m-Z \qquad (XIV)$$

in which m has the same meaning as in formula I, and Z has the same meaning as in formula III, under the conditions of a nucleophilic substitution as described under process variant (a), to give compounds of the formula XV, followed by conversion of the hydroxyl group into the leaving group Y by customary methods

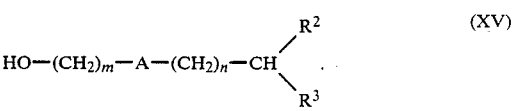

The compounds of the formula VIII are known or can be obtained by straightforward processes from starting materials which can be bought.

The compounds of the formula IX

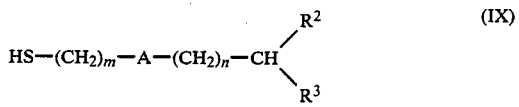

in which $R^2$, $R^3$, A, m and n have the same meaning as in formula I, can be prepared from compounds of the formula III by reaction with compounds of the formula XVI

in which m has the same meaning as in formula I, and Y has the same meaning as in formula II, under the conditions of a nucleophilic substitution as described under process variant (a), or from the compounds of the formula V by reaction with a compound of the formula XVII

in which m has the same meaning as in formula I, and Z has the same meaning as in formula III, under the conditions of a nucleophilic substitution as described under process variant (a), or from the compounds of the formula VII by substitution of the leaving group Y by a mercapto group by one of the customary methods.

The compounds of the formula X are prepared using the general processes of protective group chemistry from the compounds of the formula III, or from the compounds of the formula V by reaction with protected amines, as has already been described for the preparation of compounds of the formula III from those of the formula V.

The compounds of the formula XI are prepared using the general processes of protective group chemistry from the compounds of the formula IV, or from the compounds of the formula VI by reaction with compounds of the formula XII, as has already been described for the preparation of compounds of the formula IV from those of the formula VI.

The compounds of the formula XII are prepared using the general processes of protective group chemistry from the compounds of the formula XIII, or by reaction of $\alpha,\omega$-dihalogenoalkanes or $\omega$-halogenoalkyl sulfonates with protected amines, as has already been described for the preparation of compounds of the formula III from those of the formula V.

The compounds of the formula XV can be prepared from compounds of the formula III by reaction with compounds of the formula XVIII

in which m has the same meaning as in formula I, and Y has the same meaning as in formula II, under the conditions of a nucleophilic substitution as described under process variant (a), or from the compounds of the formula V by reaction with a compound of the formula XIV, as has been described for the preparation of compounds of the formula VII from those of the formula V.

The compounds of the formulae XIII, XIV, XVI, XVII and XVIII are known or can be obtained by straightforward processes from starting materials which can be bought.

The compounds of the formula I, according to the invention, exhibit biological actions, in particular calcium-antagonistic actions, and thus have valuable properties for the treatment of all disease states which derive from a disturbance of the calcium balance: in particular they are suitable as agents to lower blood pressure, agents having antianginal effects, agents having antiarrhythmic effects, and for improving cerebrovascular blood flow.

Their calcium-antagonistic activity can be shown in the biochemical test model of displacement of tritium-labeled nitrendipine. We carried out this test in a membrane preparation obtained from the cortex of the rat brain and washed several times, the method which we used being essentially that of R. J. Gould et al. (Proc. Natl. Acad. Sci. USA 79, 3656 [1982]). The membrane suspension which had been diluted 1:1500 with TRIS buffer pH 7.4 (50 mM TRIS-HCl, 150 mm NaCl, 1.0 mM $CaCl_2$ and 0.001% by weight, based on TRIS-HCl, NaCl and $CaCl_2$ solution, of a neutral surface-active substance such as, for example, Genapol ®) was incubated in 5 ml portions with $^3$H-nitrendipine (0.1 nM in the test, specific activity 81.3 Ci/mMol) and with the test substances in various concentrations in a shaking water bath at 25° C. for 60 min. The membrane fractions were removed by vacuum filtration through Whatman GF/F fiber glass filters, and the radioactivity was measured in a liquid scintillation counter. We determined the unspecific $^3$H-nitrendipine binding in the presence of 1 $\mu$M nifedipine. The $IC_{50}$ is determined as characteristic quantity, i.e. the concentration of test substance which is able to displace 50% of the radiolabeled nitrendipine.

The $IC_{50}$ values of the compounds of the formula I, according to the invention, in this model are from about $10^{-6}$ molar to about $10^{-9}$ molar. Thus, they have distinctly greater activity than known comparison compounds such as flunarizine and lidoflazine.

The table which follows contains some of the measured $IC_{50}$ values

| Example No. | $IC_{50}$ ($10^{-9}$ M) |
| --- | --- |
| 1 | 4 |
| 2 | 20 |
| 3 | 7 |
| 4 | 22 |
| 5 | 1.2 |
| Flunarizine | 1000 |
| Lidoflazine | 430 |

The compounds of the formula I likewise have high activity in other test models with which it is possible to detect a calcium-antagonistic action, for example in the relaxant action on the previously contracted guinea pig ileum, in the action potential of the isolated guinea pig papillary muscle, or in the action on the coronary flow in the isolated guinea pig heart.

The compounds of the formula I, according to the invention, and their pharmacologically tolerated salts are active within a wide dose range. The level of the dose administered depends on the nature of the desired treatment, on the mode of administration, on the condition, on the type and on the size of the treated patient. On oral dosage, satisfactory results are achieved with doses of 0.01 mg upwards, preferably from 0.1 mg up to 100 mg, preferably up to 20 mg, of a compound of the formula I per kg of body weight. In humans the daily dose varies between 1 and 800 mg, preferably from 2 to 500 mg, it being possible to give single doses of from 0.5 to 200 mg, preferably once to three times a day. The dose for intravenous and intramuscular administration is 0.1 to 300 mg, preferably 0.5 to 150 mg, each day.

The pharmacologically utilizable compounds of the present invention, and their salts, can be used for the preparation of pharmaceutical products which contain an effective amount of the active substance together with vehicles, and which are suitable for enteral and parenteral administration. It is preferable to use tablets or gelatin capsules which contain the active substance together with diluents, for example lactose, dextrose, sucrose, mannitol, sorbitol, cellulose and/or glycine, and lubricants such as diatomaceous earth, talc, stearic acid or its salts, such as magnesium or calcium stearate, and/or polyethylene glycol. Tablets additionally contain binders such as magnesium aluminum silicate, starch, gelatin, tragacanth, methylcellulose, sodium carboxymethylcellulose and/or polyvinylpyrrolidone and, if necessary, colorants, flavorings and sweeteners. Injectable solutions are preferably isotonic aqueous solutions or suspensions which can be sterilized and can contain auxiliaries such as preservatives, stabilizers, wetting agents and/or emulsifiers, solubilizers, salts to control the osmotic pressure and/or buffer substances. The pharmaceutical products according to the invention which, if desired, can contain additional pharmacologically valuable substances, are prepared, for example, by conventional mixing, granulating and coating processes and contain 0.1% to about 75%, preferably about 1% to about 50%, of the active substance.

The examples which follow are intended to illustrate the invention without confining it to these examples.

EXAMPLE 1

1-[4,4-bis(4-fluorophenyl)butyl]-4-[2-(4-chlorophenylthio)ethyl]piperazine

A solution of 1.15 g (8 mmol) of 4-chlorothiophenol in 20 ml of absolute dimethylformamide was slowly added dropwise to a suspension of 0.35 g of sodium hydride (55% dispersion in oil) in 8 ml of absolute dimethylformamide, and the mixture was heated at 40° C. for one hour. After the evolution of gas had finished, the mixture was heated at 60° C. for a short time, then cooled to room temperature and a solution of 3.05 g (7.7 mmol) of 1-[4,4-bis(4-fluorophenyl)butyl]-4-(2-chloroethyl)piperazine in 25 ml of absolute dimethylformamide was added, and the mixture was stirred at room temperature for 24 hours. The solution was added to 110 ml of 0.2N sodium hydroxide solution, the mixture was extracted with methylene chloride, the extract was dried over magnesium sulfate and concentrated, and the product was purified by column chromatography on silica gel (toluene/ethanol 9:1). Yield: 2.6 g (67%) of oily product. The crystalline dihydrochloride was obtained by dissolving this oil in ethyl acetate and treatment with ethereal HCl, melting point 244° C. (decomposition).

The following products were obtained by an analogous preparation route.

EXAMPLE 2

1-[4,4-bis(4-fluorophenyl)butyl]-4-[2-(4-methylphenylthio)ethyl]piperazine dihydrochloride, melting point 235°–238° C.

EXAMPLE 3

1-[4,4-bis(4-fluorophenyl)butyl]-4-[2-(4-fluorophenylthio)ethyl]piperazine dihydrochloride, melting point 230°–233° C.

EXAMPLE 4

1-[4,4-bis(4-fluorophenyl)butyl]-4-[2-(4-nitrophenylthio)ethyl]piperazine dihydrochloride, melting point 223°–233° C.

EXAMPLE 5

1-[4,4-bis(4-fluorophenyl)butyl]-4-[2-(3-chlorophenylthio)ethyl]piperazine dihydrochloride, melting point 239°–249° C.

We claim:

1. A compound of the formula I $$R^1-S-(CH_2)_m-A-(CH_2)_n-CH\begin{matrix}R^2\\R^3\end{matrix}\quad (I)$$

in which

R$^1$ denotes (C$_1$–C$_6$)-alkyl, straight-chain or branched, (C$_3$–C$_8$)-cycloalkyl, (C$_2$–C$_6$)-alkenyl, straight-chain or branched, (C$_5$–C$_8$)-cycloalkenyl,

[phenyl ring with substituents R$^4$, R$^5$, R$^6$]

in which

R$^4$, R$^5$ and R$^6$ denote, identically or differently and independently of one another, hydrogen, (C$_1$–C$_6$)-alkyl, (C$_3$–C$_8$)-cycloalkyl, hydroxyl, (C$_1$–C$_4$)-alkoxy, (C$_1$–C$_4$)-alkylthio, F, Cl, Br, I, nitro, cyano, trifluoromethyl, formyl, carboxyl, (C$_1$–C$_6$)-alkoxycarbonyl, (C$_1$–C$_6$)-acyl, carbamoyl, N-mono- or N,N-di-(C$_1$–C$_6$)-alkylcarbamoyl, sulfo, (C$_1$–C$_6$)-alkoxysulfonyl, sulfamoyl, N-mono- or N,N-di-(C$_1$–C$_6$)-alkylsulfamoyl, (C$_1$–C$_6$)-alkylsulfinyl, (C$_1$–C$_6$)-alkylsulfonyl, or amino, unsubstituted or substituted with one or two identical or different ·(C$_1$–C$_6$)-alkyl, (C$_1$–C$_6$)-acyl or phenyl groups, R$^2$ and R$^3$ denote, identically or differently and independently of one another, phenyl or phenyl-(C$_1$–C$_4$)-alkyl, the phenyl ring in each case being unsubstituted or substituted by one, two or three substituents from the group consisting of (C$_1$–C$_4$)-alkyl, (C$_1$–C$_4$)-alkoxy, F, Cl, Br, I, cyano, nitro and trifluoromethyl, A denotes an amine $$-N\underset{(CH_2)_p}{\overset{R^8}{\diagup\diagdown}}N-$$

in which

R$^8$ denotes hydrogen, (C$_1$–C$_6$)-alkyl, formyl, (C$_1$–C$_6$)-acyl, carboxyl, (C$_1$–C$_6$)-alkoxycarbonyl, carbamoyl, N-mono- or N,N-di-(C$_1$–C$_6$)-alkylcarbamoyl, p denotes 2, m denotes 2, 3 or 4, and n denotes 1, 2, 3 or 4, or a salt of said compound of the formula I with a physiologically tolerated acid.

2. A compound of the formula I as claimed in claim 1, in which the radicals and indices have the following meaning:

$R^1$ denotes $(C_3-C_8)$-cycloalkyl,

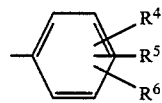

in which $R^4$, $R^5$ and $R^6$ denote, identically or differently and independently of one another, hydrogen, $(C_1-C_6)$-alkyl, $(C_1-C_4)$-alkoxy, $(C_1-C_4)$-alkylthio, F, Cl, Br, I, nitro, cyano, trifluoromethyl, formyl, carboxyl, $(C_1-C_6)$-alkoxycarbonyl, $(C_1-C_6)$-acyl, carbamoyl, N-mono- or N,N-di-$(C_1-C_6)$-alkylcarbamoyl, sulfo, sulfamoyl, N-mono- or N,N-di-$(C_1-C_6)$-alkylsulfamoyl, $(C_1-C_6)$-alkylsulfinyl or $(C_1-C_6)$-alkylsulfonyl, $R^2$ and $R^3$ denote, identically or differently and independently of one another, phenyl or phenylmethyl, the phenyl ring in each case being unsubstituted or substituted by one, two or three substituents from the group consisting of methyl, ethyl, methoxy, ethoxy, F, Cl, Br, I, cyano, nitro and trifluoromethyl, A denotes an amine

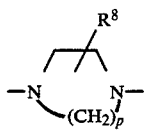

in which $R^8$ denotes hydrogen, carboxyl or carbamoyl, p denotes 2, m denotes 2, 3 or 4, and n denotes 1, 2, 3 or 4, or a salt of said compound of the formula I with a physiologically tolerated acid.

3. A compound of the formula I as claimed in claim 1, in which the substituents and indices have the following meaning:

$R^1$ denotes $(C_5-C_7)$-cycloalkyl,

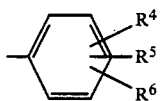

in which $R^4$, $R^5$ and $R^6$ denote, identically or differently and independently of one another, hydrogen, methyl, ethyl, propyl, isopropyl, n-butyl, sec-butyl, isobutyl, tert.butyl, methoxy, ethoxy, methylthio, fluorine, chlorine, bromine, iodine, nitro, cyano, trifluoromethyl, acetyl, methylsulfonyl or methylsulfinyl, $R^2$ and $R^3$ denote, identically or differently and independently of one another, phenyl or phenylmethyl, in each case the phenyl ring being unsubstituted or substituted by one, two or three substituents from the group consisting of methyl, fluorine, chlorine, bromine, cyano, nitro and trifluoromethyl, A denotes an amine

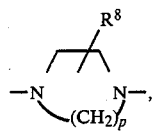

in which $R^8$ denotes hydrogen, carboxyl or carbamoyl, p denotes 2, m denotes 2, 3 or 4, and n denotes 2, 3 or 4, or a salt of said compound of the formula I with a physiologically tolerated acid.

4. A compound of the formula I as claimed in claim 1, in which the substituents and indices have the following meaning:

$R^1$ denotes

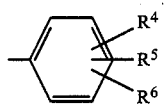

in which $R^4$, $R^5$ and $R^6$ denote, identically or differently and independently of one another, hydrogen, methyl, tert.butyl methoxy, methylthio, fluorine, chlorine, bromine, nitro, cyano, trifluoromethyl, acetyl, methylsulfonyl or methylsulfinyl, $R^2$ and $R^3$ denote, identically or differently and independently of one another, phenyl or phenylmethyl, in each case the phenyl ring being unsubstituted or substituted by fluorine or trifluoromethyl, A denotes an amine

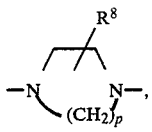

in which $R^8$ denotes hydrogen, p denotes 2, m denotes 2, and n denotes 3, or a salt of said compound of the formula I with a physiologically tolerated acid.

5. A medicine for the treatment of cardiovascular and cerebrovascular disorders, which contains an effective amount of a compound I as claimed in claim 1.

6. A method for the treatment of at least one disorder selected from cardiovascular and cerebrovascular disorders in a patient in need thereof comprising the administration to said patient of a pharmaceutically effective amount of a compound of formula I or physiologically tolerated acid salt thereof as claimed in claim 1.

* * * * *